US00PP08680P

United States Patent [19]

Austin

[11] Patent Number: Plant 8,680

[45] Date of Patent: Apr. 12, 1994

[54] ROSE PLANT 'AUSSAUCER'

[75] Inventor: David C. H. Austin, Albrighton, England

[73] Assignee: David Austin Roses Limited, Albrighton, England

[21] Appl. No.: 954,962

[22] Filed: Sep. 30, 1992

[51] Int. Cl.[5] ..... A01H 5/00

[52] U.S. Cl. ..... Plt./1

[58] Field of Search ..... Plt. 1, 25

*Primary Examiner*—Howard J. Locker
*Assistant Examiner*—E. F. McElwain
*Attorney, Agent, or Firm*—Klarquist, Sparkman, Campbell, Leigh and Whinston

[57] ABSTRACT

A brush rose variety having highly scented flowers, mixture of yellow and apricot in flowers, dwarfer habit than the variety Graham Thomas, and very quartered, regular flowers.

1 Drawing Sheet

The present invention relates to a new and distinct variety of bush rose plant of the Rosa hybrida class which was originated by me by crossing the variety Graham Thomas, with the variety Tamora.

The primary objective of this breeding was to produce a new rose variety having apricot, quartered, scented flowers on a bushy plant which repeatedly flower. The objective was substantially achieved along with other desirable improvements as evidenced by the following unique combination of characteristics which are outstanding in the new variety and which distinguish it from its parents, as well as from all other varieties of which I am aware:

1. Highly scented flowers;
2. Mixture of yellow and apricot in flowers;
3. Dwarfer habit than Graham Thomas; and
4. Very quartered, regular flowers.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Methuen Handbook of Colour, except where ordinary dictionary significance of color is indicated.

Parentage:

*Seed parent.*—Graham Thomas.

*Pollen parent.*—Tamora.

Classification:

*Botanical.*—Rosa hybrida.

*Commercial.*—Shrub.

FLOWER

Observations made from specimens grown in a garden environment in Albrighton, Wolverhampton, England in August 1991.

Blooming habit: Recurrent.

Bud:

*Size.*—1" long when the petals start to unfurl.

*Form.*—The bud form is pointed and globular, with cuspidate apex.

*Color.*—When sepals first divide, the bud color is bronwish violet 11D7 to pale orange 5A3. When half blown, the upper sides of the petals are generally pale orange 5A3, and pale yellow 3A3 in the center; and the lower isdes of the petals are light orange 6A4 at the top, and light yellow 3A5 in the center.

*Sepals.*—Color: Greyish green 29D7 with brownish violent blush 11D6 Surface texture: Slightly ridged, slightly glandular. There are three normally appendaged sepals. There are two unappendaged sepals with hairy edges.

*Receptacle.*—Color: Deep green 29D8. Shape: Apple. Size: Medium, about ¼-⅜"×¼-⅜" long. Surface: Smooth.

*Peduncle.*—Length: Medium, averaging about 1¼-1½". Surface: Glandular. Color: Light green, bronzy, greyish green 29D7 to brownish red blush 10D8. Strength: Erect.

Bloom:

*Size.*—Medium. Average open size is 2¾" to 3½" diameter.

*Borne.*—Singly, several together in clusters of up to 6 flowers. If the clusters: Flat, irregular shape.

*Stems.*—Normal. Average length is about 30 to 36 inches.

*Form.*—When first open: Bloom is cupped. Permanence: Flattens, outer petal edges curl slightly.

*Petalage.*—Number of petals under normal conditions: 80 to 100.

*Color.*—The upper side of the petals is pale orange 6A3 at the top, and pastel yellow 3A4 at the center. The reverse side of the petals is pastel red 7A4 at the top, and light yellow 3A4–4A4 at the center. The base of the petals is yellow 3A7. The major color on the upper side is pastel yellow 3A4.

*Variegations.*—None.

*Discoloration.*—The general tonality at the end of the first day: fades slightly. At the end of the third day, it is white-yellowish white 9A1 to 3A2.

*Fragrance.*—Strong.

Petals:

*Texture.*—Thick, silky.

*Shape.*—Deltoid, heart-shaped, cupped.

*Form.*—Tips slightly recurved.

*Arrangement.*—Informal, apex of inner petals caught into receptacle with few, small petaloids in the center.

*Persistence.*—Petals hang on and dry.

*Lastingness.*—On the plant: Long, fair, 7 to 10 days. As a cut flower: Long, 5 to 7 days.

Reproductive parts:

*Anthers.*—Size: Medium. Quantity: Many. Color: Reddish yellow 4A7. Arrangement: Tucked in calyx or partly so, mixed with petaloids.

*Filaments.*—Color: Reddish yellow 4A6.

*Pollen.*—Color: Gold yellow.

*Styles.*—Color: Pale green 30A3.

*Stigmas.*—Color: Greenish white, greeny yellow 1A4.

Form: Shrub.

Growth: Medium, branching, bushy.

Height: 42" to 48".

Foliage: Number of leaflets on normal mid-stem leaves: 5

*Size.*—1¾" long ×1¼" wide.

Quantity.—Normal.

*Color.*—New foliage: Green 30E7-8 and violet brown blush 11E8. Old foliage: Dark green 27F8.

Leaflets:

*Shape.*—Base is oval, cuspidate apex.

*Texture.*—Upper side: Smooth.

*Edge.*—Serrated.

*Serration.*—Single, small.

*Petiole rachis.*—Color: Green, reddish.

*Petiole underside.*—With prickles, 0 to 1 per internode, very small.

*Stipules.*—Medium, about 1" long.

*Disease resistance.*—Resistant to mildew and blackspot under normal growing conditions at Albrighton, Wolverhampton, England.

Wood:

*New wood.*—Color: Medium green 29E7-8, reddish, and violet brown blush 10F7. Bark: Smooth.

*Old wood.*—Color: Green. Bark: Smooth.

Prickles:

*Quantity.*—On main canes from base: Ordinary. On laterals from main canes: Ordinary.

*Form.*—Medium, straight.

*Color when young.*—Red.

*Position.*—Evenly spaced along stem.

Small prickles:

*Quantity.*—On main stalks: None. On laterals: None.

I claim:

1. A new and distinct variety of bush rose plant of the Rosa hybrida class, substantially as herein shown and described, characterized particularly as to novelty by the unique combination of its highly scented flowers, mixture of yellow and apricot in flowers, dwarfer habit than the variety Graham Thomas, and very quartered, regular flowers.

* * * * *

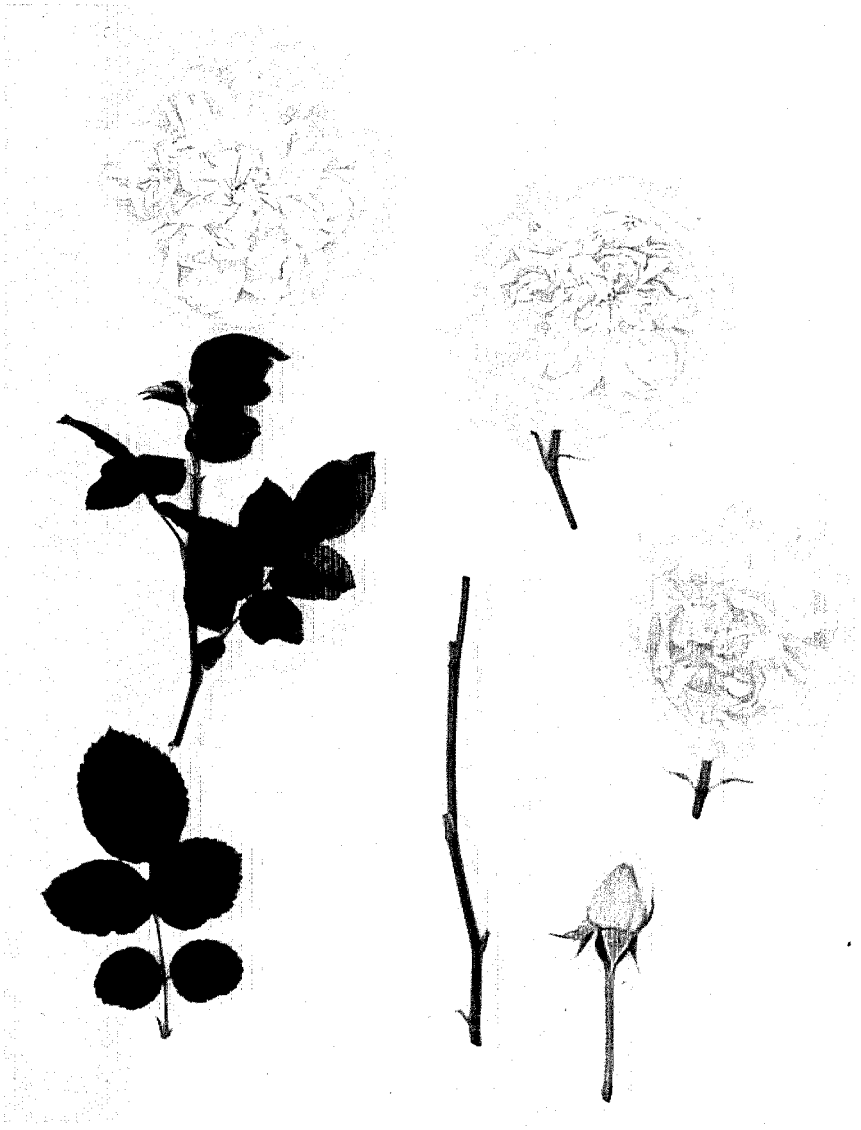

UNITED STATES PATENT AND TRADEMARK OFFICE

CERTIFICATE OF CORRECTION

PATENT NO. : PP 8,680

DATED : April 12, 1994

INVENTOR(S) : David C.H. Austin

It is certified that error appears in the above-identified patent and that said Letters Patent is hereby corrected as shown below:

In the Abstract:

Line 1, "brush" should read --bush--.

Column 2, line 4, "bronwish" should read --brownish--.

Column 2, line 7, "isdes" should read --sides--.

Column 2, line 26, "If the clusters" should read --If in clusters--.

Signed and Sealed this

Fifteenth Day of November, 1994

Bruce Lehman

BRUCE LEHMAN

*Commissioner of Patents and Trademarks*

*Attest:*

*Attesting Officer*